US005152996A

United States Patent [19]

Corey et al.

[11] Patent Number: 5,152,996

[45] Date of Patent: Oct. 6, 1992

[54] NONWOVEN WIPES IMPREGNATED WITH AN AQUEOUS SOLUTION OF A ZINC ACETATE PEROXIDE AND A SURFACTANT

[75] Inventors: Garland G. Corey, Milltown; Robert W. Bender, Jersey City, both of N.J.

[73] Assignee: Eastman Kodak Company, Rochester, N.Y.

[21] Appl. No.: 624,837

[22] Filed: Dec. 10, 1990

[51] Int. Cl.[5] .......................... A61K 9/70; D04H 1/64; D04H 1/58

[52] U.S. Cl. ...................................... 424/443; 15/208; 252/8.6; 252/8.8; 252/528; 424/401; 424/404; 424/409; 424/411; 424/446

[58] Field of Search ............... 424/401, 443, 404, 446, 424/411, 409; 252/528, 8.6, 8.8; 428/289; 15/208

[56] References Cited

U.S. PATENT DOCUMENTS

| | | | |
|---|---|---|---|
| 3,817,702 | 6/1974 | Paulus et al. | 424/443 X |
| 4,172,841 | 10/1979 | Danna et al. | 556/131 |
| 4,199,322 | 4/1980 | Danna et al. | 8/186 |
| 4,336,151 | 6/1982 | Like et al. | 252/528 X |
| 4,615,937 | 10/1986 | Bouchette | 424/443 X |
| 4,847,088 | 7/1989 | Blank | 424/443 X |
| 4,865,844 | 9/1989 | Blank et al. | 424/409 |
| 4,941,989 | 7/1990 | Kramer et al. | 424/446 X |

*Primary Examiner*—Thurman K. Page
*Assistant Examiner*—Robert H. Harrison
*Attorney, Agent, or Firm*—John R. Everett

[57] ABSTRACT

An antibacterial aqueous composition comprising a) a zinc acetate complex characterized in that the composition also contains b) from 0.1% by weight to 1.0% by weight of a selected surfactant is disclosed. Nonwoven wipes containing such composition is also disclosed.

7 Claims, No Drawings

NONWOVEN WIPES IMPREGNATED WITH AN AQUEOUS SOLUTION OF A ZINC ACETATE PEROXIDE AND A SURFACTANT

FIELD OF THE INVENTION

The present invention relates to antibacterial compositions and nonwoven wipes containing such compositions.

BACKGROUND OF THE INVENTION

Various forms of impregnated nonwoven fabrics are available for performing a wide variety of tasks such as cleaning hard surfaces, cleaning hands and other areas of the body and delivery active antibacterial agents to various surfaces both animate and inanimate. Such fabrics are marketed as wipes ready for use either in individual packet form or in bulk form in suitable dispensers from which individual wipes can be withdrawn as needed. Whatever the form of packaging, the wipes are stored for substantial period of time prior to use. Antibacterial nonwoven substrates are described for example in U.S. Pat. Nos. 3,786,615; 4,395,454 and 4,199,322.

U.S. Pat. No. 4,172,841 discloses a process for imparting antibacterial activity to cellulosic and polyester textiles. The textiles are treated with an aqueous solution which contains 1% to 30% by weight of zinc acetate and 1% to 30% of hydrogen peroxide. At zinc acetate concentrations of 5% or greater, the solution also contains 1% to 25% of acetic acid. The textiles are subsequently heated to drive off water and acetic acid, thereby converting the water-soluble reagents to insoluble peroxide complexes of zinc acetate deposited on the textile.

The treatment is applicable to unfinished textiles and also to cellulosic textiles having a durable press finish. The treatment inhibits the growth and spreading of odor- and infection-producing bacteria on the textile. The antibacterial activity imparted is durable to repeated laundering.

While the antibacterial nonwoven material provided by the latter patent is 100% effective against gram-negative organisms such as *salmonella choleraesuis* (*s. choleraesuis*), it is less effective against gram-positive organisms such as *staphylococcus aureus* (*S. aureus*).

SUMMARY OF THE INVENTION

The present invention provides premoistened, nonwoven fabric which contains a composition that is 100% effective against gram-negative organisms and more effective than the above previously disclosed zinc acetate peroxide complex (ZAP) against gram-positive organisms.

The essence of the present invention provides an aqueous composition comprising a) a zinc acetate complex characterized in that the composition also contains b) from 0.1% by weight to 1.0% by weight of a surfactant selected from the group:

i) a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride;

ii) n-alkylbenzene sulfonates sodium salt wherein alkyl has average of of 11 carbon atoms;

(iii) cocoamphocarboxypropionate; and (iv) lauryl diethanolamine oxide.

In a preferred embodiment of the above composition a) the zinc acetate complex is formed from 5 to 30 weight percent of zinc acetate, from 1 to 30 weight percent of hydrogen peroxide and from 1 to 25 weight percent acetic acid and the surfactant b) is selected from the group:

i) a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride; and ii)n-alkylbenzene sulfonates sodium salt wherein alkyl has average of of 11 carbon atoms.

DETAILS OF THE INVENTION

The zinc acetate complex (ZAP) is prepared according to the teachings of U.S. Pat. No. 4,172,841, which is incorporated herein by reference. The zinc acetate used may be either the anhydrous salt or the more widely available dihydrate having the formula $Zn(OOCCH_3)_2 2H_2O$. In the description that follows, all percentages are by weight and refer to the anhydrous compound, except where specifically stated otherwise.

Zinc acetate reacts with hydrogen peroxide in aqueous media to form solid, colorless, water-insoluble complexes whose elemental analyses correspond to the structure:

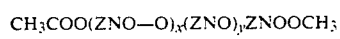

$$CH_3COO(ZNO{-}O)_x(ZNO)_yZNOOCH_3$$

where x has values in the range of 9–16, and y has values in the range of 1–7. The value of x and y vary with the proportions of zinc acetate and hydrogen peroxide used in carrying out the reaction. The analyses indicate that these water-insoluble products are polymeric complexes derived from three simple compounds; namely zinc peroxide, zinc oxide and zinc acetate.

The reaction to form these complexes proceeds to completion only if the water present as solvent, and the acetic acid formed as co-product, are removed by evaporation. The evaporation can be hastened by heating the mixture at atmospheric pressure or under partial vacuum in the range of 0.1 to 1 atmosphere.

It is preferable to carry out the reaction in the presence of excess hydrogen peroxide, especially since some hydrogen peroxide may be lost through volatilization during the evaporation step. At zinc acetate concentrations of less than 5% (or less than 6% calculated as zinc acetate dihydrate) mixing of zinc acetate, hydrogen peroxide and water yields slightly hazy but still reasonably uniform and usable solutions. At higher concentrations of zinc acetate, however, precipitates of ZAP complexes appear. This precipitation can be prevented and even reversed by the addition of 0.2–3.0 parts by weight of acetic acid per part of zinc acetate, to give an acetic acid concentration of 1%–25%

The addition of acetic acid is essential when it is desired to apply the ZAP as a concentrated uniform, homogenous solution to textile materials. Such addition can also be advantageous in preparing batches of the solid complexes themselves, since a non uniform product results when the composition of the initially precipitated solids differs from that of solids subsequently formed as evaporation proceeds. The use of acetic acid for this purpose has the advantage that this acid is volatile and readily removed by vaporization along with the water present. Evaporation to dryness converts the water-soluble reagents to the desired water-insoluble complexes.

The preferred weight ratios of acetic acid to zinc acetate are in the range of 0.2 to 3.0 for the textile treatment as well as for the preparation of the complexes, but other ratios are operative. The preferred order of addition in preparing the treating solution is that of adding the acetic acid to a mixture of zinc acetate and 25% to 50% aqueous hydrogen peroxide, and finally adding the water. However, this order is optional and examples of the inverse order of addition are included below.

The purpose of heating the impregnated textile is to drive off water and acetic acid by volatilization, and to convert the water soluble zinc acetate and hydrogen peroxide to water-insoluble complexes deposited in the textile material in a form resistant to removal by subsequent laundering. The peroxide complexes are stable to temperatures of 50° C. to 120° C. for long periods of time. Final drying can be carried out by an ordinary means such as oven drying, line drying, or tumble drying in a mechanical clothes dryer. High temperatures, in excess of 140° C. for long periods, should be avoided to ensure against thermal decomposition of the complexes in the textile finish. A drying temperature of 80° C. to 120° C. for 1-5 minutes is particularly preferred.

Depending on the particular use intended for a wipe impregnated with the aqueous composition of the invention, optional ingredients may be included in the aqueous composition.

Thus a wipe intended for cleansing the skin may include skin moisturizers/humectants such as propylene glycol, glycerin and sorbitol; skin softeners/emollients such as ethoxylated lanolin, ethoxylated glucose, silicone oils, mineral oil and fatty acid esters; botanical extracts such as witch hazel extract, aloe vera gel and chamomile extract; and perfumes and fragrances. The concentrations of such optional ingredients will, based on the weight of the final composition, fall in the ranges of 0.2 to 10 weight-percent for skin moisturizers and humectants, 0.02 to 5 weight-percent for skin softeners and emollients, 0.01 to 50 weight-percent for botanical extracts and 0.01 to 2 weight-percent for perfumes and fragrances.

Other surfactants and cleanser optionally may also be included in the aqueous compositions of the invention.

The substrate employed in the moistened wipe of the invention is a fibrous flexible absorbent nonwoven sheet material consisting essentially of cellulosic fibers or blends of cellulosic fibers such as rayon and cotton fibers or blends of such cellulosic fibers with one or more synthetic fibers such as polypropylene, polyethylene, polyester and nylon fibers. Such blends may also include wood pulp fibers. Binders generally are employed to bind together the fibers thus ensuring that the finished nonwoven sheet has adequate wet strength. Such binders are, for example, acrylic polymers, ethylene vinyl acetate polymers, vinyl acetate copolymers and styrene butadiene polymers. Such nonwoven materials and processes for their manufacture are well known in the art. Processes for manufacturing such nonwoven sheet materials include carding, air laying, water entanglement, thermal bonding and wet laying.

EXAMPLES OF THE INVENTION

The following examples demonstrate the improved effectiveness of the composition of the present invention against gram positive organisms. In the examples, unless stated otherwise, the nonwoven wipes tested were prepared by immersing about 50 grams of nonwoven paper stock into 200 grams of composition solution for about 5 to 10 minutes, rotating the wipes until full saturation occurs. The wipes were then removed from the composition solution bath and hand squeezed to remove excess solution. The wipes were then hung to air dry at ambient temperature overnight. Then the paper stock was rinsed in tap water, squeezed by hand and dried in a commercial clothes drier at about 65 degrees centigrade for about 1 hour. These wipes were then examined for antimicrobial activity.

The solution bath in which the wipes were treated was prepared by dissolving 32 grams of zinc acetate and 26.4 grams of glacial acetic acid in 86.4 grams of water at ambient room temperature. Then 59.2 grams of hydrogen peroxide (50%) was added. The surfactants used in the compositions of the invention were then added as necessary.

EXAMPLE 1

Disinfectant Wipe Test

Treated and untreated nonwoven wipes were tested for germicidal activity against Salmonella choleraesuis ATCC#10708 with 5% horse serum and Staphylococcus aureus ATCC#6538 with 5% horse serum by a Disinfectant Wipe Protocol and Zone of Inhibition test. The purpose of this test was to compare the disinfectant capabilities of ZAP complex treated wipes also containing surfactants according to this invention with those wipes treated with the ZAP complex only. The results are summarized below:

| Control | Composition Tested: Zinc Peroxide Acetate (ZAP) Complex Wipes |
|---|---|
| 1 | ZAP Complex + 1.0% n-alkylbenzene sulfonates sodium salt wherein alkyl has average of 11 carbon atoms (Witco Sulfamin 1240 slurry available from Witco Chemical) |
| 2 | ZAP Complex + 1.0% lauryl diethanol amino oxide (Ammonyx LO available from Stepan Chem.) |
| 3 | ZAP Complex + 1.0% of a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride (BTC-2125 M available from Stepan) |
| 4 | ZAP Complex + 1.0% cocoamphocarboxypropionate (CFTA adopted name available as Miranol C2MSF from Mirano Chemical Co.) |

Methodology

Disinfectant Wipe Protocol

Ten 77.4/m$^2$ (12") squares pieces of heavy-duty aluminum foil per sample per microorganism were sterilized in a hot air oven for two hours and then used as the unit area to be wiped. To each piece, a 6.452 cm$^2$ (1") square in the middle of the foil was inoculated with 0.03 ml of S. aureus or S. choleraesuis each with 5% horse serum and dried for 30 minutes at 37° C. After drying, two 25.8 cm$^2$ (4") squares containing the inoculated square in the center was aseptically cut and immediately transferred to subculture jars of letheen broth as the dry controls. Each of the ten 25.8 cm$^2$ (4") squares containing the inoculated areas was wiped with the treated wipes for 10 seconds. The 25.8 cm$^2$ (4") square area of two pieces of foil was wiped with the wet, untreated (water) wipe for 10 seconds. All wipes were soaked in 4.0 ml of sterile water for suitable wetness prior to wiping. After 10 minutes contact period, each 25.8 $cm^2$ (4") square piece of foil containing the inoculated square was cut and subcultured into jars of letheen broth. All used wipes were subcultured into bottles of letheen broth. Plate counts were done on all subcultured jars and bottles and plates were incubated at 37° C. for 48 hours.

In the disinfectant wipe test, the control wipes treated with zinc peroxide acetate complex (ZAP) exhibited a 100% reduction of S choleraesuis and a 95.64% reduction of S aureus. Wipes treated with a) ZAP+1.0% Witco Sulfamin and b) ZAP+1.0% Active BTC 2125M exhibited a comparable reduction of 100% against S. choleraesuis and an increased reduction of 99.85% and 100%, respectively, against S. aureus when compared with the control treated wipes; c)ZAP+1.0% Active Ammonyl LO and d) ZAP+1.0% Active Miranol $C_2$MSF treated wipes demonstrated a very slight decrease in reduction against S. choleraesuis of 99.995% and 99.991% respectively, and an increase in activity against S. aureus with a reduction determination of 99.73% and 96.07% respectively, when compared with the control treated wipes.

The above described average percent reduction of bacterial on foil and wipe for the dried inoculum is reported in Table I.

TABLE I

| Treated Test Wipe | Average Percent Reduction of Bacterial or Foil and Wipe Fan Dried Inocolum Organism | |
|---|---|---|
| | *S. chloeraesuis* | *S. aureus* |
| Control (ZAP Complex) | 100 | 95.64 |
| 1) ZAP + 1% WITCO Sulfamin 1240 | 100 | 99.85 |
| 2) ZAP + 1.0% BTC 2125M | 100 | 100 |
| 3) ZAP + 1.0% Ammonyx LO | 99.995 | 99.73 |
| 4) ZAP + 1% Active Miranol $C_2$MSF Wipes | 99.99 | 96.07 |

EXAMPLE 2

The objective of this example was to ascertain the effects of ZAP, in combination with a surfactant carefully selected for use in the compositions of the invention, upon the release rate of the surfactant and the peroxide when the substrate after treatment was placed into water.

SAMPLES & PREPARATIONS

Control 1

A roll of nonwoven fabric (available from Lehn & Fink), total weight of 50 grams, with each sheet averaging 0.68 grams) was immersed in 200 ml water solution containing 10,000 ppm the quaternary surfactant BTC-2125M. The material after soaking for approximately 30 minutes was removed, wrung by hand and allowed to air dry overnight.

Control 2

The same procedure was utilized as in Control 1 with the exception that after air drying overnight, the sample was rinsed in tap water for approximately 10 minutes, then placed into a clothes dryer and tumble dried for 30–45 minutes at between 71° to 79.5° C. (160°–175° F.) with forced air.

A) A sample of the invention was prepared as Sample Control 2 with the exception that the treatment solution contained the ZAP complex wherein the hydrogen peroxide was 15%.

B) This sample according to the invention was prepared as in Control 2 with the exception that the treatment solution contained the ZAP complex with hydrogen peroxide at 15%, in addition to the 10,000 ppm of quaternary surfactant BTC 2125-M already present.

C) This sample according to the invention was prepared as Sample Control 2 except the BTC 2125-M was replaced with SULFAMIN 1240 Slurry.

Sample nonwoven sheets (initial dry weight of each sheet averaging 0.68 g) from the above prepared stocks were then placed in distilled water (200 ml) and analytically examined for surfactant and hydrogen peroxide after 10 minutes, 1 hour, and 2 hours.

Table II below outlines the results obtained by quaternary titration.

TABLE II

| Sample | % Quaternary Surfactant in Treatment Solution (200 ml) | % Surfactant in Elution | | |
|---|---|---|---|---|
| | | 10 min | 1 hr | 2 hr |
| Control 1 | 1.0 (10,000 ppm) | 0.537 | 0.599 | 0.716 |
| | " | 0.714 | 0.804 | 0.893 |
| | " | 0.788 | 0.912 | 0.912 |
| Control 2 (Rinsed) | 1.0 (10,000 ppm) | 0.008 | 0.008 | 0.005 |
| | " | 0.008 | 0.007 | 0.008 |
| | " | 0.008 | 0.008 | 0.008 |
| B | 1.0 (10,000 ppm) | 1.04 | 1.38 | 1.35 |

The results above indicate the following:

a) Comparing Control 2 with Sample B, since both were prepared in an identical manner, a greater return of the quaternary surfactant back into solution is disclosed for B.

b) In comparing samples Control 1 to Control 2 wherein the sample was simply dried after immersion, more quaternary surfactant was recovered in 1 than in 2.

c) Comparing more quaternary surfactant was recovered in sample B, even though the B sample had gone through a rinsing step.

Table III below outlines the peroxide titration results:

TABLE III

| Sample | % $H_2O_2$ in Treatment Solution (200 ml) | % $H_2O_2$ in Elution after | | |
|---|---|---|---|---|
| | | 10 min | 1 hr | 2 hr |
| A | 15% | 0.12 | 0.17 | 0.17 |
| B | 15% + 10,000 ppm BTC 2125-M | 0.27 | 0.35 | 0.38 |
| C | 15% + 10,000 ppm alkyl benzene sulfonate | 0.13 | 0.18 | 0.22 |

The results above indicate that the addition of both surfactants improve release rate of the peroxide into solution over the control. This allows for greater potential for reducing microorganisms than observed with the prior art zinc acetate peroxide complex alone. The utility of our invention results in a nonwoven wipe releasing antimicrobial activity when wetted and that dried gauze or bandages will exist with built in antimicrobial activity.

The testing reported in Table III above was made by removing an aliquot proportion of the sample water.

The aliquot was then treated with sulfuric acid to liberate the available oxygen.

EXAMPLE 3

Inoculation and incubation of treated fabrics with *Trichophyton mentagrophytes*, a fungus active in causing ringworm of the feet and hands, was carried out in a manner analogous to the disinfectant wipe protocol described above. Treated, unlaundered fabrics showed substantially decreased fungal growth as compared to untreated fabric, and even after twenty laundering cycles, the treated fabric still showed moderately decreased fungal growth.

The invention has been described in detail with particular reference to preferred embodiments thereof, but it will be understood that variations and modifications can be effected within the spirit and scope of the invention.

We claim:

1. A moistened, fibrous, flexible, nonwoven sheet material, consisting essentially of cellulosic fibers or blends of cellulosic fibers, impregnated with an aqueous composition comprising a zinc acetate peroxide complex and from 0.1% to 1.0% by weight of a surfactant selected from the group consisting of:

i) a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride;

ii) n-alkylbenzene sulfonates sodium salt wherein alkyl has an average of 11 carbon atoms;

iii) cocoamphocarboxypropionate; and iv) lauryl diethanolamine oxide.

2. The moistened fibrous, flexible, nonwoven sheet of claim 1 wherein a) the zinc acetate complex is formed from 1 to 30 weight percent of zinc acetate, from 1 to 30 weight percent of hydrogen peroxide and from 1 to 25 weight percent acetic acid and the surfactant b) is selected from composition is selected from the group consisting of:

i) a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride;

ii) n-alkylbenzene sulfonates sodium salt wherein alkyl has average of 11 carbon atoms.

3. The moistened fibrous, flexible, nonwoven sheet of claim 1 wherein the weight percent of acetic acid is 0.2 to 3.0.

4. The moistened fibrous, flexible, nonwoven sheet of claim 2 or 1 wherein the surfactant b) is present in an amount of at least 1% by weight of the total solution.

5. The moistened fibrous, flexible, nonwoven sheet of claim 2 or 1 wherein the zinc acetate complex is formed from about 32 g of zinc acetate, about 26.4 g of acetic acid and about 59.2 g of hydrogen peroxide combined with 2.0 g of the surfactant.

6. The moistened fibrous, flexible, nonwoven sheet of claim 1 wherein the surfactant is a 1:1 mixture, by weight, of n-alkyl (60% $C_{14}$, 30% $C_{16}$, 5% $C_{12}$, 5% $C_{18}$) dimethyl benzyl ammonium chloride and N-alkyl (68% $C_{12}$, 32% $C_{14}$) dimethylethylbenzyl ammonium chloride.

7. A moistened, fibrous, flexible, nonwoven sheet according to claims 2, 3 or 1 also wherein the sheet includes a binder.

* * * * *